United States Patent
Kwok et al.

(10) Patent No.: US 7,178,527 B2
(45) Date of Patent: Feb. 20, 2007

(54) NASAL MASK AND MASK CUSHION THEREFOR

(75) Inventors: Philip Rodney Kwok, Chatswood (AU); Robert Edward Styles, Glenhaven (AU)

(73) Assignee: ResMed Limited, Bella Vista (AU)

( * ) Notice: Subject to any disclaimer, the term of this patent is extended or adjusted under 35 U.S.C. 154(b) by 215 days.

(21) Appl. No.: 10/068,963

(22) Filed: Feb. 11, 2002

(65) Prior Publication Data
US 2002/0074001 A1 Jun. 20, 2002

Related U.S. Application Data

(63) Continuation of application No. 09/230,491, filed as application No. PCT/AU97/00450 on Jul. 16, 1997, now Pat. No. 6,357,441.

(30) Foreign Application Priority Data
Jul. 26, 1996 (AU) ...................... PO1265

(51) Int. Cl.
*A62B 18/02* (2006.01)
(52) U.S. Cl. .................... 128/207.13; 128/205.25; 128/206.18; 128/206.24
(58) Field of Classification Search ........... 128/206.24, 128/206.25, 207.11, 207.13, 206.4
See application file for complete search history.

(56) References Cited

U.S. PATENT DOCUMENTS

| 781,516 A | 1/1905 | Guthrie |
|---|---|---|
| 812,706 A | 2/1906 | Warbasse |

(Continued)

FOREIGN PATENT DOCUMENTS

| AU | 64058/86 | 4/1987 |
|---|---|---|
| AU | 91/77110 B | 11/1991 |
| AU | 94/64816 B | 12/1994 |
| AU | 95/16178 B | 7/1995 |
| AU | 9459430 | 2/1996 |

(Continued)

OTHER PUBLICATIONS

"ResMed Sullivan Mirage—The Mirage is Real—A Perfect Fit—First Time," product brochure © ResMed Limited 1997, 4 pages.

(Continued)

*Primary Examiner*—Anhtuan T. Nguyen
*Assistant Examiner*—Darwin P Erezo
(74) *Attorney, Agent, or Firm*—Nixon & Vanderhye P.C.

(57) ABSTRACT

A nasal cushion (30) comprises a substantially triangularly shaped frame (32) from which extends a membrane (34). The frame (32) has a scalloped edge (36) by which the cushion (30) is affixed to a mask body. The membrane (34) has an aperture (38) into which the wearer's nose is received. The membrane (34) is spaced away from the rim (40) of the frame (32), and its outer surface (41) is of substantially the same shape as the rim (40). Respective notches (42, 44) receive the bridge of the wearer's nose. The wearer's nose is received through the aperture (38) into the chamber within the mask body (46). The seal forming portion (45) thus contacts both the surface of the wearer's nose and a portion of the wearer's face in the region between the base of the nose and the upper lip, and around the sides and over the bridge of the nose. The shape of the seal forming portion (45) is particularly suited to effectively seal the difficult region of the facial contour that is the crease between between the sides of the nose and the face.

96 Claims, 3 Drawing Sheets

U.S. PATENT DOCUMENTS

| | | | |
|---|---|---|---|
| 902,961 A | 11/1908 | Goodnow | |
| 1,000,706 A | 8/1911 | Barnum | |
| 1,081,745 A | 12/1913 | Johnston et al. | |
| 1,192,186 A | 7/1916 | Greene | |
| 1,206,045 A | 11/1916 | Smith | |
| 1,653,572 A | 12/1927 | Jackson | |
| 1,653,592 A | 12/1927 | Jackson | |
| 1,926,027 A | 9/1933 | Biggs | |
| 2,123,353 A | 7/1938 | Catt | |
| 2,166,164 A | 7/1939 | Lemberg | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,465,973 A | 3/1949 | Bulbulian | |
| 2,578,621 A | 11/1951 | Yant | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,182,659 A | 5/1965 | Blount et al. | |
| 3,189,027 A | 6/1965 | Bartlett | |
| 3,193,624 A | 7/1965 | Webb et al. | |
| 3,227,159 A | 1/1966 | Borgia et al. | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,521,630 A | 7/1970 | Westberg et al. | |
| 3,556,122 A | 1/1971 | Laerdal | |
| 3,580,051 A | 5/1971 | Blevins | |
| 3,680,555 A | 8/1972 | Warncke | |
| 3,700,000 A | 10/1972 | Hesse et al. | |
| 3,720,235 A | 3/1973 | Schrock | |
| 3,796,216 A | 3/1974 | Schwarz | |
| 3,799,164 A | 3/1974 | Rollins | |
| D231,803 S | 6/1974 | Huddy | |
| 4,077,404 A | 3/1978 | Elam | |
| D250,131 S | 10/1978 | Lewis et al. | |
| 4,167,185 A | 9/1979 | Lewis | |
| 4,174,710 A | 11/1979 | Pampuch | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,328,797 A | 5/1982 | Rollins et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,414,973 A | 11/1983 | Matheson et al. | |
| 4,454,880 A | 6/1984 | Muto et al. | |
| 4,467,799 A | 8/1984 | Steinberg | |
| 4,522,639 A | 6/1985 | Ansite et al. | |
| 4,558,710 A | 12/1985 | Eichler | |
| 4,574,799 A | 3/1986 | Warncke | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| H397 H | 1/1988 | Stark | |
| D293,613 S | 1/1988 | Wingler | |
| 4,739,755 A * | 4/1988 | White et al. | 128/206.12 |
| 4,770,169 A | 9/1988 | Schmoegner et al. | |
| 4,774,941 A | 10/1988 | Cook | |
| 4,782,832 A | 11/1988 | Trimble et al. | |
| 4,794,921 A | 1/1989 | Lindkvist | |
| 4,799,477 A | 1/1989 | Lewis | |
| 4,803,981 A | 2/1989 | Vickery | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Bellm | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,003,633 A | 4/1991 | Itoh | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,148,802 A * | 9/1992 | Sanders et al. | 128/204.18 |
| 5,159,938 A | 11/1992 | Laughlin | |
| 5,178,138 A | 1/1993 | Walstrom et al. | |
| D334,633 S | 4/1993 | Rudolph | |
| 5,220,699 A | 6/1993 | Farris | |
| 5,231,983 A | 8/1993 | Matson et al. | |
| 5,233,978 A | 8/1993 | Callaway | |
| 5,243,971 A * | 9/1993 | Sullivan et al. | 128/205.25 |
| 5,265,595 A | 11/1993 | Rudolph | |
| 5,279,289 A | 1/1994 | Kirk | |
| 5,280,784 A | 1/1994 | Kohler | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |

| | | | | | | |
|---|---|---|---|---|---|---|
| 5,546,936 A | 8/1996 | Virag et al. | | EP | 0 821 978 | 2/1998 |
| RE35,339 E | 10/1996 | Rapoport | | FR | 2 574 657 A1 | 6/1986 |
| 5,560,354 A | 10/1996 | Berthon-Jones et al. | | FR | 2 658 725 A1 | 8/1991 |
| 5,570,682 A | 11/1996 | Johnson | | FR | 2 749 176 | 12/1997 |
| 5,570,689 A | 11/1996 | Starr et al. | | GB | 1395391 | 5/1975 |
| D377,089 S | 12/1996 | Starr et al. | | GB | 1 467 828 | 3/1977 |
| 5,592,938 A | 1/1997 | Scarberry et al. | | GB | 2145335 A | 3/1985 |
| 5,608,647 A | 3/1997 | Rubsamen et al. | | GB | 2147506 A | 5/1985 |
| 5,642,730 A | 7/1997 | Baran | | GB | 2 164 569 A | 3/1986 |
| 5,647,355 A | 7/1997 | Starr et al. | | GB | 2 267 648 A | 12/1993 |
| 5,647,357 A | 7/1997 | Barnett et al. | | JP | 44-16955 | 7/1969 |
| 5,649,532 A | 7/1997 | Oren | | JP | 09/216240 A | 8/1997 |
| 5,649,533 A | 7/1997 | Griffiths | | WO | WO 80/01044 | 5/1980 |
| 5,655,520 A | 8/1997 | Howe et al. | | WO | WO 82/03548 | 10/1982 |
| 5,655,527 A | 8/1997 | Scarberry et al. | | WO | WO 86/06969 | 12/1986 |
| 5,657,493 A | 8/1997 | Ferrero et al. | | WO | WO 87/01950 | 4/1987 |
| 5,657,752 A | 8/1997 | Landis et al. | | WO | WO 91/03277 | 3/1991 |
| 5,662,101 A | 9/1997 | Ogden et al. | | WO | WO 92/15353 | 9/1992 |
| 5,666,946 A | 9/1997 | Langenback | | WO | WO 92/20395 | 11/1992 |
| 5,685,296 A | 11/1997 | Zdrojkowski et al. | | WO | WO 93/01854 | 2/1993 |
| 5,687,715 A | 11/1997 | Landis et al. | | WO | WO 94/02190 | 2/1994 |
| 5,715,814 A | 2/1998 | Ebers | | WO | WO 94/16759 | 8/1994 |
| 5,724,965 A | 3/1998 | Handke et al. | | WO | WO 94/20051 | 9/1994 |
| 5,746,201 A | 5/1998 | Kidd | | WO | WO 95/02428 | 1/1995 |
| 5,813,423 A | 9/1998 | Kirchgeorg | | WO | WO 96/17643 | 6/1996 |
| 5,832,918 A | 11/1998 | Pantino | | WO | WO 96/25983 | 8/1996 |
| 5,884,624 A | 3/1999 | Barnett et al. | | WO | WO 96/39206 | 12/1996 |
| 5,921,239 A | 7/1999 | McCall et al. | | WO | WO 97/07847 | 3/1997 |
| 6,082,360 A | 7/2000 | Rudolph et al. | | WO | WO 97/41911 | 11/1997 |
| 6,112,746 A | 9/2000 | Kwok et al. | | WO | WO 98/04310 | 2/1998 |
| 6,119,693 A | 9/2000 | Kwok et al. | | WO | WO 98/11930 | 3/1998 |
| 6,357,441 B1 | 3/2002 | Kwok et al. | | WO | WO 98/18514 | 5/1998 |
| 6,412,487 B1 | 7/2002 | Gunaratnam et al. | | WO | WO 98/24499 | 6/1998 |
| 6,513,526 B2 * | 2/2003 | Kwok et al. ............ 128/206.24 | | WO | WO 98/26829 | 6/1998 |
| 6,581,602 B2 | 6/2003 | Kwok et al. | | WO | WO 98/26830 | 6/1998 |
| 6,634,358 B2 * | 10/2003 | Kwok et al. ............ 128/205.25 | | WO | WO 98/48878 | 11/1998 |
| 6,701,927 B2 * | 3/2004 | Kwok et al. ............ 128/207.13 | | | | |
| 2004/0094159 A1 | 5/2004 | Kwok et al. | | | | |

FOREIGN PATENT DOCUMENTS

| | | |
|---|---|---|
| AU | A 32914/95 | 2/1996 |
| AU | A 41018/97 | 4/1998 |
| AU | A 89312/98 | 1/1999 |
| CA | 1039144 | 9/1928 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 195 48 380 A1 | 12/1994 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 | 7/1987 |
| EP | 0 264 772 | 10/1987 |
| EP | 0 303 090 | 7/1988 |
| EP | 0 386 605 A1 | 2/1990 |
| EP | 0 462 701 A1 | 5/1991 |
| EP | 0427474 A2 | 5/1991 |
| EP | 0 602 424 | 11/1993 |
| EP | 0 608 684 A1 | 8/1994 |
| EP | 0 634 186 A2 | 1/1995 |
| EP | 0 697 225 | 7/1995 |
| EP | 178 925 A2 | 4/1996 |
| EP | 0 747 078 A2 | 12/1996 |

OTHER PUBLICATIONS

Mirage Spare Parts Brochure, 1997, 2 pages.
Mask 1 Photographs, Respironics Inc., Reusable Full Mask (small) Part # 452033 Lot #951108.
Mask 2 Photographs, Puritan—Bennett, Adam Curcuit , Shell Part # 231700, Swivel Part # 616329-00, Pillows (medium) Part #616324.
Mask 3, Photographs, DeVilbiss Healthcare Inc., DeVilbiss Seal-Ring and CPAP Mask Kit (medium), Part 73510-669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510-668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.
U.S. Appl. No. 10/704,754, filed Nov. 2003, Kwok et al.

* cited by examiner

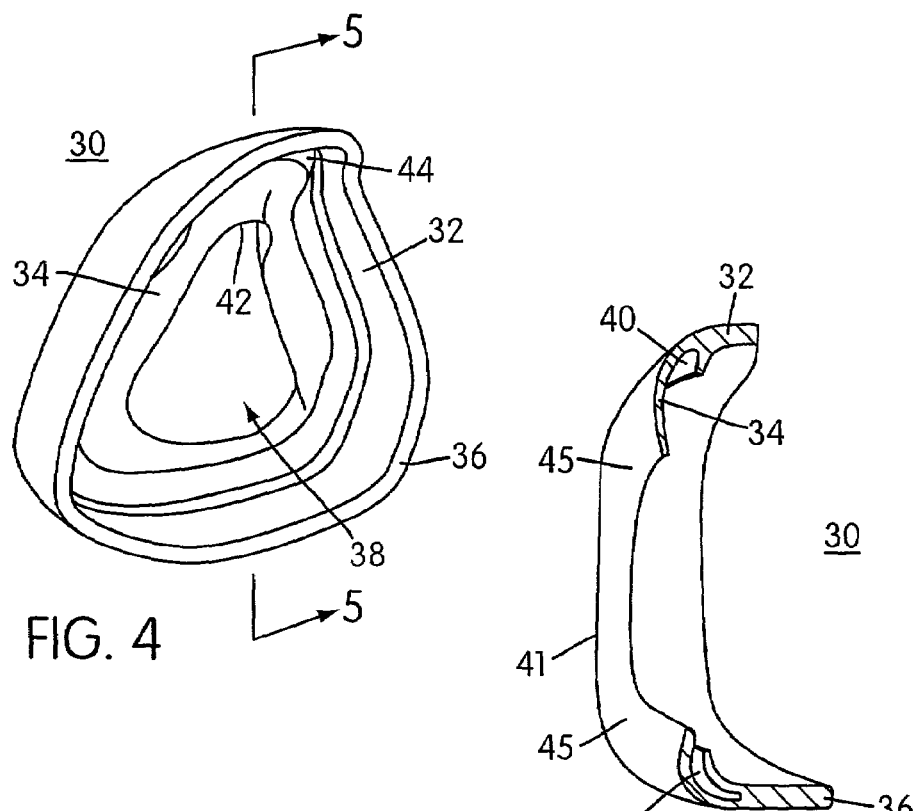
FIG. 4
FIG. 5
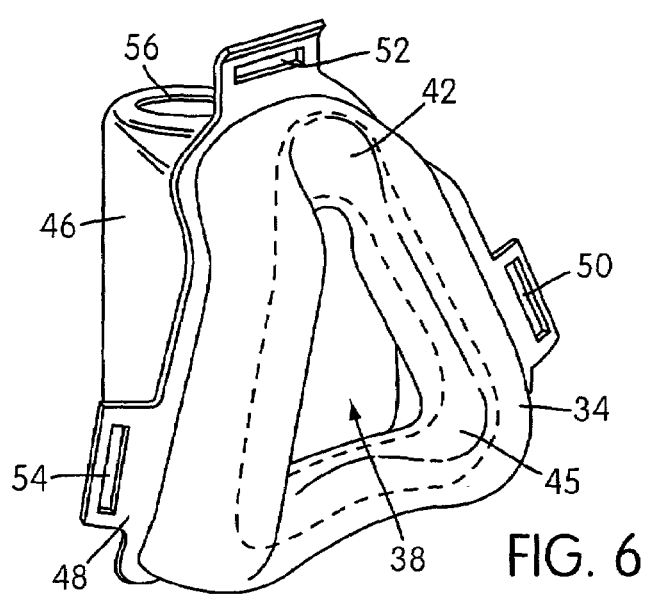
FIG. 6

NASAL MASK AND MASK CUSHION THEREFOR

CROSS REFERENCE TO RELATED APPLICATIONS

This application is a continuation of U.S. Application Ser. No. 09/230,491, filed Aug. 11, 1999, now U.S. Pat. No. 6,357,441 the specification and drawings of which is incorporated herein by reference. Application Ser. No. 09/230,491 claims priority to Australian Provisional Patent Application No. PO1265, filed Jul. 26, 1996, through 371 PCT Application No. PCT/AU97/00450, filed Jul. 16, 1997 (published as WO 98/04310 on 5 Feb. 1998). This application contains subject matter related to U.S. Application Ser. No. 08/791,212, filed Jan. 31, 1997, now U.S. Pat. No. 6,112,746, incorporated by reference in its entirety, which also claims priority to Australian Provisional Patent Application No. PO1265, filed Jul. 26, 1996.

FIELD OF THE INVENTION

The invention relates generally to a nasal mask and to a cushion therefor, for example, for use in the treatment of respiratory conditions and in assisted respiration.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask. The walls usually are semi-rigid and have a face contacting portion including an aperture which is aligned with the wearer's nostrils. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This excessive forces. In some cases these excessive pressures and forces may cause the face to distort to conform with the face contacting portion to increase wearer discomfort, facial soreness and ulceration.

Other types of devices exist whereby small nostril nosepieces (pillows) are held in place by a harness strapped over the wearer's head, for example as shown in prior art U.S. Pat. No. 4,782,832. While this arrangement may alleviate some problems regarding seal breakage and skin abrasion, the harnesses associated with such devices are quite cumbersome for the wearer, as are the gas supply lines. Also, air 'jetting' into the nostrils can be irritating to the patient making such devices generally uncomfortable to use.

In FIGS. 1–3, a prior art nasal cushion 10, generally equivalent to that shown in prior art U.S. Pat. No. 5,243,971, is first described.

As shown, the cushion 10 generally includes a base 11 from which depends a semi-rigid cushion frame 12 formed of elastomeric material. Attached over the outside of the frame 12 is a membrane 15, also of elastomeric material, having at its distal end a face contacting portion 14. The frame 12 and the membrane 15 generally form a chamber 17 into which the wearer's nose can be received. The frame 12 has a notch 19 to accommodate the bridge of the wearer's nose. The base 11 includes slots 13 to accommodate straps (not shown) to secure the cushion 10 and a mask body (not shown) in combination to the wearer's head.

An aperture 16 is formed at the end of the membrane 15 distal from the frame 12 providing access for a wearer's nose 20 to the chamber 17 as noted. As shown, the aperture 16 in an unflexed state is generally circular (or elliptical) and is large enough to allow partial entry of the wearer's nose. The resilience of the membrane material allows the face contacting portion 14 and the aperture 16 to invert when the nose is received. The inverted membrane arrangement relies upon a positive pressure of supplied gas within the mask to effect a seal to the wearer's face. The seal is characterised as a "rolling edge seal", in that there can be motion of the cushion 10 relative to the patient's face yet the seal is maintained. Even so, a tuck 22 arises in the vicinity of the upper lip due to the circular shape of the aperture, and it is from this tuck that leaks can arise due to head and body movement during sleep.

It is an object of the invention to overcome or at least substantially ameliorate one or more of the foregoing disadvantages.

SUMMARY OF THE INVENTION

In one broad form, the invention discloses a nasal mask cushion to sealingly connect a mask to a wearer's face, the cushion comprising:

a substantially triangularly-shaped frame of resilient material having a rim to surround the wearer's nose;

a membrane also of resilient material, the membrane being relatively more flexible than the frame, and being of the same general shape as said rim and fixed to and extending away from the frame so as to have an outer surface spaced from the rim, a portion of said outer surface forming a face contacting seal; and a nose-receiving cavity bounded by said frame and said membrane;

and wherein said seal portion is generally coterminous with respect to said rim and is resiliently deformable towards the rim in use of the cushion.

Preferably, the rim and seal portion are shaped to generally match facial contours of the facial tissue around the sides and over the bridge of the nose and between the base of the nose and the top lip.

In one particularly advantageous form, the membrane is substantially saddle-shaped. The membrane further has a centrally located aperture through which the wearer's nose passes to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the base of the nose and the top lip.

The invention further discloses a nasal mask for connection to a wearer's face comprising:

a mask body for connection with a supply of breathable gas; and a nasal cushion, the body and cushion defining a nose-receiving cavity, the cushion including:

a substantially triangularly-shaped frame of resilient material having a rim to surround the wearer's nose;

a membrane also of resilient material, the membrane being relatively more flexible than the frame, and being of the same general shape as said rim and fixed to and extending away from the frame so as to have an outer surface spaced from the frame, a portion of said outer surface forming a face contacting seal;

and wherein said seal portion is generally coterminous with respect to said rim and is resiliently deformable towards the rim in use of the mask.

The mask body can further include attachment points from which securing straps can be attached, and by which the mask can be secured to the wearer's head. The nasal mask can yet further comprise an arm depending from said body from which a further securing strap(s) can be attached.

The invention further discloses nasal CPAP treatment apparatus comprising a flow generator for the supply of gas at a pressure elevated above atmospheric pressure to a gas delivery conduit, the conduit in turn coupled to a nasal mask as described immediately above.

In one particularly preferred form, a supply of gas can be provided to said cavity, said supply of gas assisting, but not solely causing maintenance of a seal by said seal forming portion of said membrane to the face of the wearer in use of the cushion.

Advantageously, because the membrane and the rim are substantially shaped to the facial contour, and the membrane does not need to turn in on itself, as in the prior art, thus contacting the face without folds or creases. With the cushion/mask secured to the wearer's head, the headstraps need only to be tensioned to balance the force due to mask gas pressure that tends to lift the mask off the face. Such relatively lower mask-to-face pressure results in greater patient comfort, and a reduction in the likelihood of skin irritation.

BRIEF DESCRIPTION OF THE DRAWINGS

An embodiment of the invention will now be described with reference to the accompanying drawings, in which:

FIG. 4 is a rear perspective view of a mask cushion embodying the present invention;

FIG. 5 is a cross-sectional view along line 5—5;

FIG. 6 is a perspective view of a nasal mask including the cushion of FIGS. 4 and 5.

DESCRIPTION OF THE PREFERRED EMBODIMENTS

Figure 1:
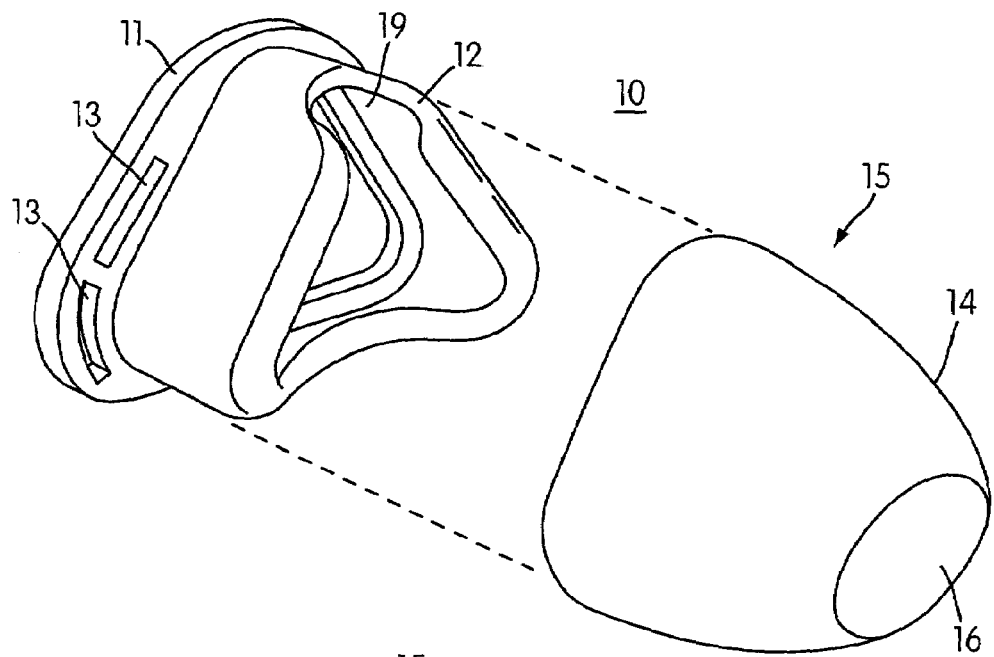
FIG. 1 is an exploded perspective view of a prior art nasal mask.

FIG. 4 shows a perspective view of a nasal cushion 30 embodying the invention. FIG. 5 shows the cross-sectional view along line 5—5. The cushion 30 comprises a substantially triangularly shaped frame 32 from which extends a membrane 34. The frame 32 has a scalloped edge 36 by which the cushion 30 is affixed to a mask body, as presently will be described.

The membrane 34 has an aperture 38 into which the wearer's nose is received in use of the cushion 30. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42,44 that receive the bridge of the wearer's nose in use of the cushion 30.

As is best seen in FIG. 5, the frame 32 and the membrane 34 are integrally formed, typically by in a one-shot molding process. The frame 32 and the membrane 34 are fabricated from a resilient material. One suitable such material is Silastic™ silicone elastomer manufactured by Dow Corning. The frame 32, in one preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the cushion 30, a wearer's nose will be inserted in the aperture 38 to engage a seal forming portion 45 (formed between the dashed lines) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the cushion 30 to tend to retain its shape and resist deformation. It thus acts as a supporting structure.

Referring now to FIG. 6, the nasal cushion 30 is shown attached to a mask body 46 by the edge 36 of the frame 32, adhered or otherwise secured to a flange 48 of the mask body 46. Only the outer surface 41 of the membrane 34 can be seen. The flange 48 includes three slots 50–54 from which tensioning straps can be attached to secure the cushion 30 and the mask body 46 (in combination) to the head of a wearer.

The mask body 46 forms a cavity that can receive the nose of the wearer by the aperture 38. A port 56 is provided at the top of the mask body 46 by which breathable gas can be supplied to the chamber.

Figure 7:
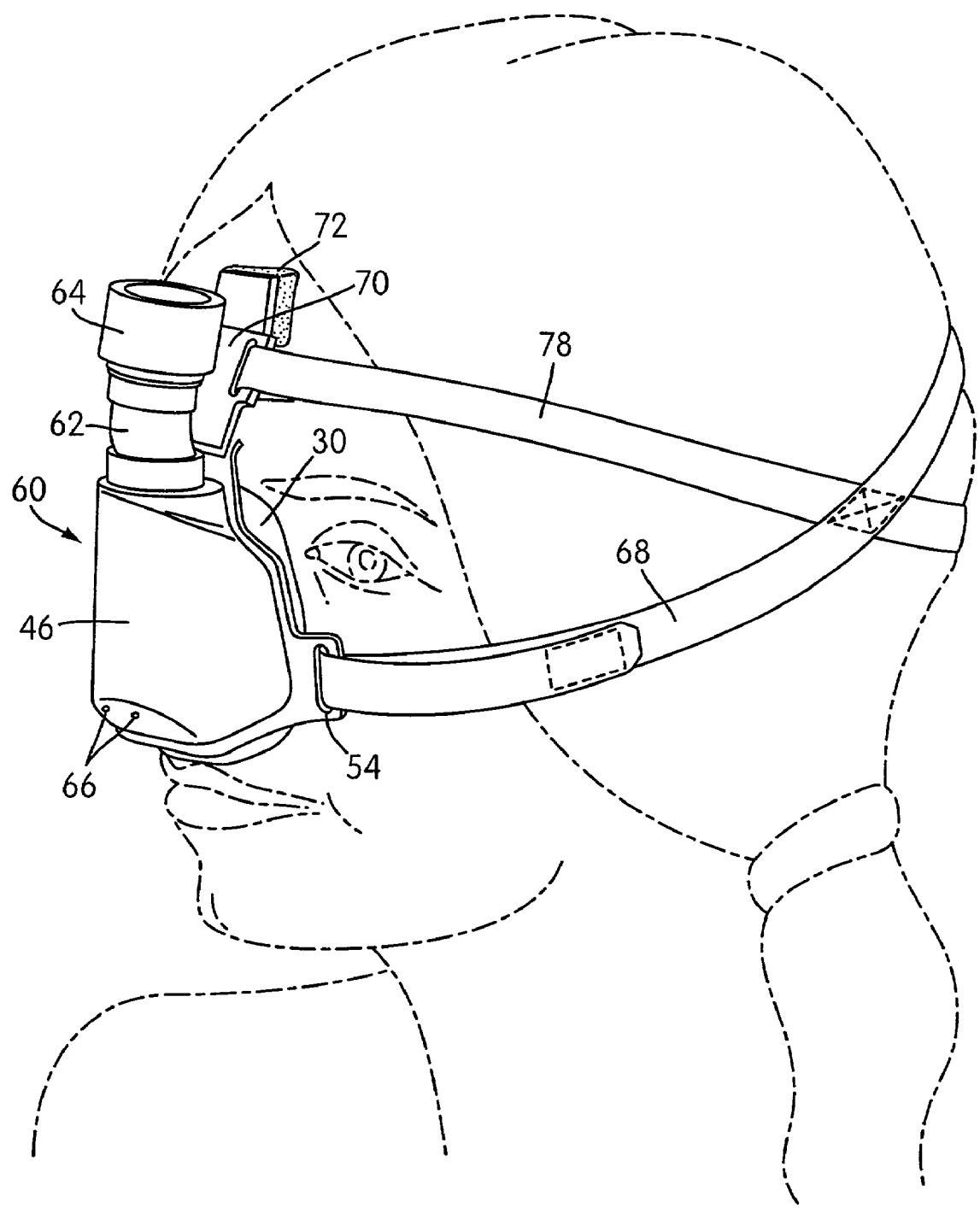
FIG. 7 is a perspective view of the nasal mask of FIG. 6 secured to a wearer's head.

Referring now to FIG. 7, there is shown a nasal mask 60 including the mask body 46 and the mask cushion 30. A coupling tube 62 is connected at one end with the inlet port 56, and at the other to a socket 64 into which can be received a gas delivery tube (not shown) for the supply of breathable gas to the chamber internal of the mask body 46. The mask body 46 also has two vent openings 66 by which expired gas is exhausted. A first fastening strap 68 is fixed between to the lower two slots 50,54. The upper slot 52 receives an arm 70, the top end of which has a resilient pad 72 to engage the forehead of the wearer. The arm 70 has two slots 74,76 along its side edges, by which a second fastening strap 78 is secured.

Figure 2:
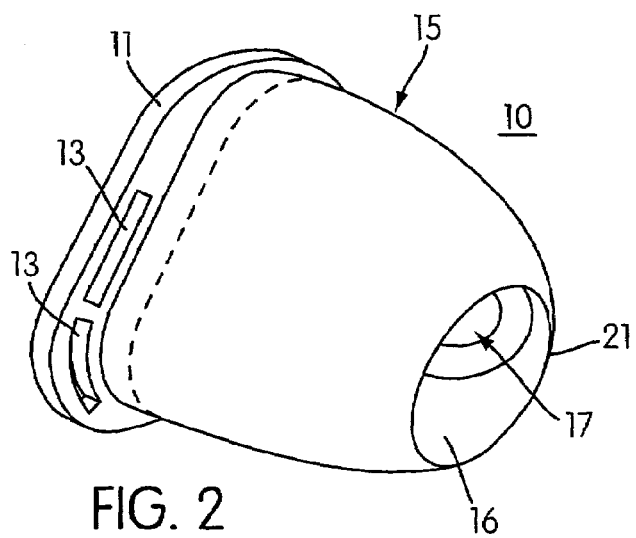
FIG. 2 is a perspective view of the prior art nasal mask of FIG. 1.
Figure 3:
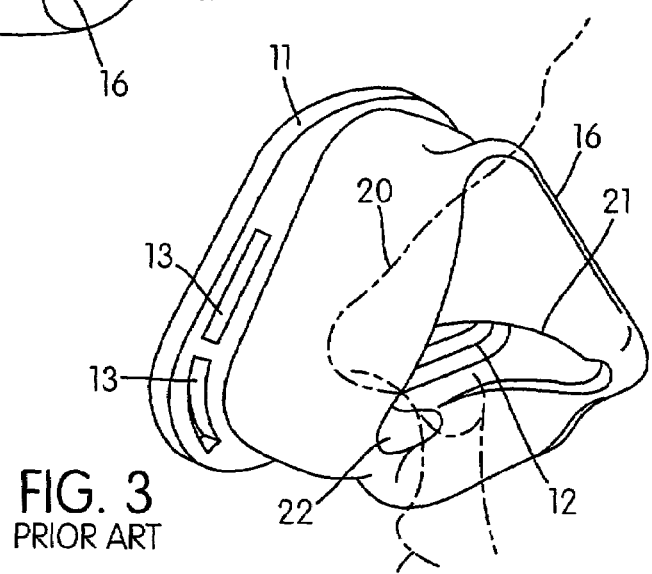
FIG. 3 is a perspective view of the prior art nasal mask attached to a wearer.

In fining the nasal mask 60, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the fastening straps 68,78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. The seal formed between the membrane 34 and the wearer's nose and face is not in the nature of a rolling seal in the manner of prior art as shown in FIGS. 1 to 3, as on relative movement of the mask 60 in relation to the wearer's head, the nose will be restrained by contacting the frame 32. Thus only limited relative motion between the mask 60 and the wearer's nose and face occurs.

The membrane 34 closely imitates the facial contour, and because of its relatively lesser stiffness than the frame 32, can conform to particular facial structures with minimum force, and without a tendency to fold or crease.

If the fastening strap 68,78 are tensioned to excess, the membrane 34 deforms to abut the rim 40 of the cushion 32, the frame 32 thus acting as an "end limit". In such a configuration, almost zero relative movement can occur between the mask 60 and the wearer's head.

The nasal cushion 30 and nasal mask 60 has been described with reference to CPAP or assisted respiration treatment, however it is to be understood that the invention generally is applicable to any application where gas and/or atomised liquid is to be supplied to the entrance of the nasal airways. Such applications include nebulisers, gas masks and anaesthetic machines.

The invention claimed is:

1. A nasal mask cushion assembly to sealingly connect a nasal mask to a wearer's face, the cushion assembly comprising:
    a generally triangularly shaped frame of resilient material, the frame including an outer surface, an inner surface having an inwardly oriented rim extending along at least a portion of a perimeter of the frame and a notch adapted to receive the bridge of the wearer's nose; and
    a generally triangularly shaped membrane of resilient material, the membrane including an aperture adapted to receive the wearer's nose, an outer surface including a seal forming portion adapted to deform and form a seal over a portion of the wearer's face when the mask is in use, an inner surface opposing the rim of the frame, an edge defining the perimeter of the aperture, and a notch in a region of the membrane adapted to receive the bridge of the wearer's nose, wherein
    the membrane is more flexible than the frame;
    the aperture of the frame is larger than the aperture of the membrane; and
    the edge of the membrane, in use, is spaced a distance from the rim in at least the region of the membrane adapted to receive the bridge of the wearer's nose.

2. A nasal mask cushion assembly according to claim 1, wherein the frame and the membrane are formed in a single piece.

3. A nasal mask cushion assembly to sealingly connect a nasal mask to a wearer's face, the cushion assembly comprising:
    a generally triangularly shaped frame of resilient material, the frame including a first side adapted to contact a mask body of the nasal mask, a second side opposite the first side, an aperture extending from the first side to the second side, a rim on the second side extending around at least a portion of the perimeter of the aperture, and a notch in the rim in a region adapted to receive the bridge of the wearer's nose; and
    a generally triangularly shaped membrane of resilient material, the membrane including an aperture adapted to receive the wearer's nose, an edge defining the perimeter of the aperture, a notch in a region adapted to receive the bridge of the wearer's nose, a first surface including a seal forming portion disposed around the perimeter of the aperture adapted to deform and form a seal over a portion of the wearer's face in a region between the base of the nose and the upper lip and around the sides and over the bridge of the wearer's nose when the mask is in use, a second surface opposite the first surface that surrounds and is spaced a first distance from the rim of the frame in at least the region adapted to receive the bridge of the wearer's nose when the mask is in use, wherein the membrane is more flexible than the frame.

4. A nasal mask cushion assembly according to claim 3, wherein the frame and the membrane are formed in a single piece.

5. A nasal mask cushion assembly according to claim 3, wherein the nasal mask cushion is adapted to fit with a human patient in use.

6. A nasal mask cushion assembly according to claim 3, wherein the nasal mask cushion comprises a CPAP cushion including a breathing chamber subject to above ambient pressure in use.

7. A nasal mask cushion assembly to sealingly connect a nasal mask to a wearer's face, the cushion assembly comprising:
    a generally triangularly shaped frame of resilient material, the frame including an inner surface including an inwardly oriented rim extending along at least a portion of a perimeter of the frame, an outer surface, an aperture, and a notch in a region adapted to receive the bridge of the wearer's nose; and
    a generally triangularly shaped membrane of resilient material, the membrane including an aperture adapted to receive the wearer's nose, an outer surface including a seal forming portion adapted to deform and form a seal over a portion of the wearer's face in a region between the base of the nose and the upper lip and around the sides and over the bridge of the wearer's nose when the mask is in use, an inner surface opposing the rim and spaced a first distance from the rim of the frame in at least the region of the frame adapted to receive the bridge of the wearer's nose when the mask is in use, an edge defining the perimeter of the aperture, and a notch in a region of the membrane adapted to receive the bridge of the wearer's nose, wherein
    the membrane is more flexible than the frame;
    the aperture of the frame is larger than the aperture of the membrane; and
    the edge of the membrane is spaced a second distance from the rim, the second distance being variable.

8. A nasal mask cushion assembly according to claim 7, wherein the frame and the membrane are formed in a single piece.

9. A nasal mask cushion assembly to sealingly connect a nasal mask to a wearer's face, the cushion assembly comprising:
    a generally triangularly shaped frame of resilient material, the frame including a first side adapted to contact a mask body of the nasal mask, a second side opposite the first side, an aperture extending from the first side to the second side, an inwardly oriented rim extending along at least a portion of a perimeter of the frame and a notch in a region adapted to receive the bridge of the wearer's nose; and a generally triangularly shaped membrane of resilient material, the membrane including an aperture adapted to receive the wearer's nose, an edge defining the perimeter of the aperture, a notch in a region adapted to receive the bridge of the wearer's nose, a first surface including a seal forming portion disposed around the perimeter of the aperture adapted to deform and form a seal over a portion of the wearer's face in a region between the base of the nose and the upper lip and around the sides and over the bridge of the wearer's nose when the mask is in use, a second surface opposite the first surface that is spaced a first distance from the rim in at least the region adapted to receive the bridge of the wearer's nose when the mask is in use, wherein the membrane is more flexible than the frame;

the aperture of the membrane is smaller than the aperture of the frame; and the edge of the membrane is spaced a second distance from the rim, the second distance being variable.

10. A nasal mask cushion assembly according to claim 9, wherein the frame and the membrane are formed in a single piece.

11. A nasal mask for connection to a wearer's face comprising:

a mask body for connection with a supply of breathable gas; and a nasal cushion secured to said mask body, the body and cushion forming a nose-receiving cavity, said cushion including:

a nasal bridge region, a cheek region and a lip region;

a first membrane of resilient material having a first molded inwardly curved rim; and a saddle-shaped second membrane also of resilient material, said second membrane having a second molded inwardly curved rim, said second molded rim being fixed to and extending away from said first membrane so as to have a second membrane inner surface spaced a distance from an outer surface of said first molded rim, said distance greater than a thickness of the first molded inwardly curved rim, said first distance measured when the mask is not in use, a portion of said second molded rim forming a face contacting seal;

wherein said face contouring, seal is substantially coterminous with respect to said second molded rim and is resiliently deformable towards said first membrane in use of said mask and, the first and second molded inwardly curved rims are curved generally towards the nose-receiving cavity.

12. The nasal mask of claim 11, further comprising an arm coupled to and extending above the nasal bridge region of the mask, the arm including an oblong slot positioned on each lateral side of the arm to receive a strap.

13. The nasal mask of claim 12, further comprising a single resilient pad mounted on the arm and centered above the nasal bridge region of the mask.

14. The nasal mask of claim 13, wherein the second membrane is conformable, in use, to various facial structures with minimum force.

15. The nasal mask of claim 14, wherein a maximum deformation position of the second membrane is defined by the first membrane.

16. The nasal mask of claim 15, wherein the maximum deformation position is not reached under normal tightening force of the mask to the wearer's face.

17. The nasal mask of claim 11, wherein the first and second membranes are formed as a one-piece unit.

18. The nasal mask of claim 11, wherein the first membrane is thicker than the second membrane.

19. The nasal mask of claim 11, wherein the mask body includes a plurality of vent openings.

20. The nasal mask of claim 11, wherein an edge of the frame interengages with the mask body, the edge being non-planar, the edge including a nasal bridge edge region and a lip edge region that diverge away from each cheek edge region and towards the mask body.

21. A nasal CPAP treatment apparatus comprising:

a flow generator for the supply of gas at a pressure elevated above atmospheric pressure;

a gas delivery conduit coupled to said flow generator; and a nasal mask in turn coupled to said conduit, said nasal mask including:

a mask body for connection with a supply of breathable gas; and a nasal cushion secured to said mask body, the body and cushion forming a nose-receiving cavity, the cushion including:

a nasal bridge region, a cheek region and a lip region;

a first membrane of resilient material having a first membrane having a first molded inwardly curved rim; and a saddle-shaped second membrane having a second molded inwardly curved rim also of resilient material, said second membrane being fixed to and extending away from said first membrane so as to have an inner surface spaced a distance from said first molded rim, said distance greater than a thickness of the first inwardly curved rim, said distance measured when the mask is not in use, a portion of said second molded rim forming a face contacting seal;

wherein said seal portion is generally coterminous with respect to said second molded rim and is resiliently deformable towards said first membrane in use of said mask, and wherein the seal portion fully covers the first molded inwardly curved rim so that the second inwardly curved rim is positioned to provide the only seal with the wearer's face in use.

22. The apparatus of claim 21, further comprising an arm coupled to and extending above the nasal bridge region of the mask, the arm including an oblong slot positioned on each lateral side of the arm to receive a strap.

23. The apparatus of claim 22, further comprising a single resilient pad mounted on the arm and centered above the nasal bridge region of the mask.

24. The apparatus of claim 23, wherein the second membrane is conformable, in use, to various facial structures with minimum force.

25. The apparatus of claim 24, wherein a maximum deformation position of the second membrane is defined by the first membrane.

26. The apparatus of claim 25, wherein the maximum deformation position is not reached under normal tightening force of the mask to the wearer's face.

27. The apparatus of claim 21, wherein the first and second membranes are formed as a one-piece unit.

28. The apparatus of claim 21, wherein the first membrane is thicker than the second membrane.

29. A mask cushion for sealingly connecting a mask to a wearers face, comprising:
   a frame defining at least a portion of a breathing chamber, said frame being of resilient material and having a first membrane, the first membrane including a first molded inwardly curved rim disposed within the breathing chamber and extending along at least a portion of an inner perimeter of the frame, said frame having a front portion with an edge structured to be coupled to a body portion of the mask; and
   a saddle-shaped second membrane of resilient material, said second membrane having a second molded inwardly curved rim, said second membrane curved rim spaced a distance from said first membrane curved rim, said distance greater than a thickness of the first molded inwardly curved rim, said distance measured when the mask is not in use, a portion of said second membrane curved rim forming a face contacting seal, wherein
   a substantially full perimeter of the second molded inwardly curved rim is curved towards the front portion of the frame opposite the wearer's face, and
   the substantially full perimeter of the second molded inwardly curved rim is provided in covering yet spaced relation to each portion of the first molded inwardly curved rim.

30. The nasal mask cushion of claim 29, wherein the second membrane is conformable, in use, to various facial structures with minimum force.

31. The mask cushion of claim 30, wherein a maximum deformation position of the second membrane is defined by the first membrane.

32. The mask cushion of claim 31, wherein the maximum deformation position is not reached under normal tightening force of the mask to the wearer's face.

33. The mask cushion of claim 29, wherein the first and second membranes are formed as a one-piece unit.

34. The mask cushion of claim 29, wherein the first membrane is thicker than the second membrane.

35. A nasal mask cushion according to claim 29, wherein the nasal mask cushion comprises a CPAP cushion including a breathing chamber subject to above ambient pressure in use.

36. A cushion and mask assembly comprising:
   a mask including a mask shell constructed to receive a supply of breathable air, an arm extending away from the mask shell and including at least one oblong slot to receive a strap, and a resilient pad provided to the arm above a nasal bridge region of the mask; and
   a cushion having a main upstanding wall, the wall having a first end removably coupleable to the mask and a second end defining an opening into a nasal cavity formed by the mask and the cushion, at least a portion of the wall including a first membrane positioned between the first and second ends and extending inwardly onto the nasal cavity, the second end of the wall defining a saddle-shaped second membrane adapted to form a seal over a portion of the wearer's face in a region between the base of the nose and the upper lip and around the sides and over the bridge of the wearer's nose when the mask is in use, the second membrane being spaced from the first membrane a distance that is greater than a thickness of the first membrane, the first membrane having a width that is less than a distance from an intersection of the first membrane and the wall to an edge of the second membrane defining an aperture of the nasal cavity, the second membrane overhanging and covering substantially all portions of the first membrane, the first membrane acting to define a maximum deformation position of the second membrane in use.

37. The assembly of claim 36, wherein the second membrane is conformable, in use, to various facial structures with minimum force.

38. The assembly of claim 36, wherein the first and second membranes are formed as a one-piece unit.

39. The assembly of claim 36, wherein the first membrane is thicker than the second membrane.

40. A mask cushion to sealingly connect a mask to a wearer's face, the cushion comprising:
   a substantially triangularly-shaped frame of resilient material having an inwardly oriented rim to surround at least a portion of the wearer's nose;
   a membrane also of resilient material, the membrane being relatively more flexible than the frame, and being of the same general shape as said rim and fixed to and extending away from the frame so as to have an outer surface spaced from the rim, a portion of said outer surface forming a face contacting seal portion; and
   a nose-receiving cavity bounded by said frame and said membrane;
   wherein:
   said face contacting seal portion is generally coterminous with respect to said rim and is resiliently deformable towards the rim in use of the cushion,
   the membrane has a radius of curvature oriented towards the nose-receiving cavity, and
   a substantially full perimeter of the membrane is provided in covering yet spaced relation to each portion of the rim.

41. The cushion as claimed in claim 40, wherein said membrane and said rim each has a co-located notch to accommodate the bridge of a nose.

42. The cushion as claimed in claim 41, wherein said membrane is shaped so that said seal portion, in use, contacts at least a wearer's nose.

43. The cushion as claimed in claim 41, wherein said membrane and said rim are substantially saddle-shaped.

44. The cushion as claimed in claim 40, wherein said membrane is shaped so that said seal portion, in use, contacts at least a wearer's nose.

45. The cushion as claimed in claim 44, wherein said seal portion, in use, contacts the facial tissue around the sides and over the bridge of the nose, and between the base of the nose and the top lip.

46. The cushion as claimed in claim 40, wherein said rim and said seal portion are shaped to generally match facial contours of the facial tissue around the sides and over the bridge of the nose, and between the base of the nose and the top lip.

47. The cushion as claimed in claim 40, wherein only the membrane is adapted to contact the wearer's face in use.

48. The cushion as claimed in claim 40, wherein only a single seal is provided about the wearer's face in use.

49. The cushion as claimed in claim 40, wherein the mask cushion is adapted to fit with a human patient in use.

50. A mask cushion according to claim 40, wherein the mask cushion comprises a CPAP cushion including a breathing chamber subject to above ambient pressure in use.

51. A nasal mask cushion to sealingly connect a mask to a wearer's face, the cushion comprising:
a nasal bridge region, a cheek region and a lip region;
a first membrane comprising a frame of resilient material having a side wall and a first molded inwardly curved rim extending from said side wall; and
a saddle-shaped second membrane of resilient material, said second membrane having a second molded inwardly curved rim, said second membrane curved rim spaced a distance from said first molded inwardly curved rim, said distance being greater than a thickness of the first molded inwardly curved rim, said distance measured when the mask is not in use, a portion of said second membrane curved rim forming a face contacting seal,
wherein the second molded inwardly curved rim has a curvature oriented to present a generally convex sealing surface to the wearer's face in use.

52. The nasal mask cushion of claim 51, wherein the second membrane is conformable, in use, to various facial structures with minimum force.

53. The nasal mask cushion of claim 52, wherein a maximum deformation position of the second membrane is defined by the first membrane.

54. The nasal mask cushion of claim 53, wherein the maximum deformation position is not reached under normal tightening force of the mask to the wearer's face.

55. The nasal mask cushion of claim 51, wherein the first and second membranes are formed as a one-piece unit.

56. The nasal mask cushion of claim 51, wherein the first membrane is thicker than the second membrane.

57. The nasal mask cushion of claim 51, wherein an edge of the frame is adapted to interengage with the mask, the edge being non-planar, the edge including a nasal bridge edge region and a lip edge region that diverge away from each cheek edge region.

58. A mask cushion according to claim 51, wherein the nasal mask cushion is adapted to fit with a human patient in use.

59. A nasal mask cushion according to claim 51, wherein the nasal mask cushion comprises a CPAP cushion including a breathing chamber subject to above ambient pressure in use.

60. A nasal mask cushion to sealingly connect a mask to a wearer's face, the cushion comprising:
a nasal bridge region, a cheek region and a lip region;
a first membrane comprising a frame of resilient material having a side wall including an edge molded to a mask body and a first molded inwardly curved rim extending from the side wall; and
a saddle-shaped second membrane of resilient material, said second membrane having a second molded inwardly curved rim, a portion of said second membrane curved rim forming a face contacting seal, said second membrane curved rim spaced a sufficient distance from said first membrane curved rim such that under a normal tightening force of the mask to the wearer's face, at least a portion of the second membrane curved rim remains spaced from the first membrane curved rim,
wherein each of the first and second molded inwardly curved rims has a radius of curvature generally oriented in a direction towards the side wall.

61. The nasal mask cushion of claim 60, wherein the second membrane is conformable, in use, to various facial structures with minimum force.

62. The nasal mask cushion of claim 61, wherein a maximum deformation position of the second membrane is defined by the first membrane.

63. The nasal mask cushion of claim 62, wherein the maximum deformation position is not reached under normal tightening force of the mask to the wearer's face.

64. The nasal mask cushion of claim 60, wherein the first and second membranes are formed as a one-piece unit.

65. The nasal mask cushion of claim 60, wherein the first membrane is thicker than the second membrane.

66. A nasal mask cushion according to claim 60, wherein the nasal mask cushion is adapted to fit with a human patient in use.

67. A nasal mask cushion according to claim 60, wherein the nasal mask cushion comprises a CPAP cushion including a breathing chamber subject to above ambient pressure in use.

68. A nasal mask for connection to a wearer's face comprising:
a mask body for connection with a supply of breathable gas; and
a nasal cushion secured to said mask body, the body and cushion forming a nose-receiving cavity, said cushion including:
a nasal bridge region, a cheek region and a lip region;
a substantially triangularly-shaped first membrane of resilient material having a first molded inwardly curved rim; and
a saddle-shaped second membrane also of resilient material, said second membrane having a second molded inwardly curved rim, said second molded rim being fixed to and extending away from said first membrane so as to have a second membrane inner surface spaced a distance from an outer surface of said first molded rim, a portion of said second molded rim forming a face contacting seal;
wherein said seal portion is substantially coterminous with respect to said second molded rim and is resiliently deformable towards said first membrane in use of said mask, at least a portion of the second molded rim remaining spaced from the first molded rim when the mask is connected to the wearer's face, and
wherein the first and second molded inwardly curved rims are generally curved towards the nose-receiving cavity.

69. The nasal mask of claim 68, further comprising an arm coupled to and extending above the nasal bridge region of the mask, the arm including at least one oblong slot to receive a strap.

70. The nasal mask of claim 69, further comprising at least one pad provided to the arm above the nasal bridge region of the mask.

71. The nasal mask of claim 70, wherein the second membrane is conformable, in use, to various facial structures with minimum force.

72. The nasal mask of claim 71, wherein a maximum deformation position of the second membrane is defined by the first membrane.

73. The nasal mask of claim 72, wherein the maximum deformation position is not reached under normal tightening force of the mask to the wearer's face.

74. The nasal mask of claim 68, wherein the first and second membranes are formed as a one-piece unit.

75. The nasal mask of claim 68, wherein the first membrane is thicker than the second membrane.

76. A nasal mask according to claim 68, wherein the nasal mask cushion is adapted to fit with a human patient in use.

77. A nasal mask according to claim 68, wherein the nasal mask cushion comprises a CPAP cushion including a breathing chamber subject to above ambient pressure in use.

78. A nasal CPAP treatment apparatus comprising:
- a flow generator for the supply of gas at a pressure elevated above atmospheric pressure;
- a gas delivery conduit coupled to said flow generator; and
- a nasal mask in turn coupled to said conduit to said nasal mask including:
  - a mask body for connection with a supply of breathable gas; and
  - a nasal cushion secured to said mask body, the body and cushion forming a nose-receiving cavity, the cushion including:
  - a nasal bridge region, a cheek region and a lip region;
  - a frame of resilient material having a first membrane with an inwardly oriented rim extending along at least a portion of the frame; and
  - a saddle-shaped second membrane having a molded inwardly curved rim also of resilient material, said second membrane being fixed to and extending away from said first membrane so as to have an inner surface spaced a distance from said first membrane, a portion of said molded rim forming a face contacting seal portion with the wearer's face in use;
  - wherein said seal portion is generally coterminous with respect to said molded rim and is resiliently deformable towards said first membrane in use of said mask, at least a portion of the molded rim remaining spaced from the membrane when the mask is connected to a wearer's face.

79. The apparatus of claim 78, further comprising an arm coupled to and extending above the nasal bridge region of the mask, the arm including an oblong slot positioned one each lateral side of the arm to receive a strap.

80. The apparatus of claim 79, further comprising a single resilient pad mounted on the arm and centered above the nasal bridge region of the mask.

81. The apparatus of claim 80, wherein the second membrane is conformable, in use, to various facial structures with minimum force.

82. The apparatus of claim 81, wherein a maximum deformation position of the second membrane is defined by the first membrane.

83. The apparatus of claim 78, wherein the maximum deformation position is not reached under normal tightening force of the mask to the wearer's face.

84. The apparatus of claim 78, wherein the first and second membranes are formed as a one-piece unit.

85. The apparatus of claim 78, wherein the first membrane is thicker than the second membrane.

86. The apparatus of claim 78, wherein the mask body includes a plurality of vent openings.

87. The apparatus of claim 78, wherein an edge of the frame interengages with the mask body, the edge being non-planar, the edge including a nasal bridge edge region and a lip edge region that diverge away from each cheek edge region and towards the mask body.

88. A nasal CPAP treatment apparatus according to claim 78, wherein the nasal mask cushion is adapted to fit with a human patient in use.

89. A mask cushion for sealingly connecting a mask to a wearer's face, comprising:
- a frame defining at least a portion of a breathing chamber, said frame being of resilient material and having a first membrane, at least a portion of the first membrane including a first molded inwardly curved rim disposed within the breathing chamber; and
- a saddle-shaped second membrane of resilient material, said second membrane having a second molded inwardly curved rim forming a boundary of said breathing chamber, said second membrane curved rim spaced a distance from said first membrane curved rim, measured when the mask is not in use, a portion of said second membrane curved rim forming a face contacting seal, said second membrane curved rim spaced a sufficient distance from said first membrane curved rim such that under a normal tightening force of the mask to the wearer's face, the second membrane curved rim remains spaced from the first membrane curved rim around at least a portion of the first membrane curved rim, wherein;
- the second molded inwardly curved rim is curved in a direction towards a front portion of the frame opposite the face contacting seal, and
- a substantially full perimeter of the second membrane curved rim is provided in covering yet spaced relation to each portion of the first membrane curved rim.

90. The mask cushion of claim 89, wherein the second membrane is conformable, in use, to various facial structures with minimum force.

91. The mask cushion of claim 90, wherein a maximum deformation position of the second membrane is defined by the first membrane.

92. The mask cushion of claim 91, wherein the maximum deformation position is not reached under normal tightening force of the mask to the wearer's face.

93. The mask cushion of claim 89, wherein the first and second membranes are formed as a one-piece unit.

94. The mask cushion of claim 89, wherein the first membrane is thicker than the second membrane.

95. A mask cushion according to claim 89, wherein the mask cushion is adapted to fit with a human patient in use.

96. A mask cushion according to claim 89, wherein the mask cushion comprises a CPAP cushion including a breathing chamber subject to above ambient pressure in use.

* * * * *